United States Patent [19]
Yorita et al.

[11] Patent Number: 5,338,431
[45] Date of Patent: Aug. 16, 1994

[54] OXYGEN CONCENTRATION DETECTING APPARATUS

[75] Inventors: Hiroshi Yorita, Anjo; Toshihiko Igashira, Toyokawa; Michiyasu Moritsugu, Okazaki; Yoshiki Chujo, Mishima, all of Japan

[73] Assignees: Nippon Soken, Inc., Nishio; Toyota Jidosha Kabushiki Kaisha, Toyota, both of Japan

[21] Appl. No.: 978,076

[22] Filed: Nov. 18, 1992

Related U.S. Application Data

[63] Continuation of Ser. No. 747,030, Aug. 19, 1991, abandoned.

[30] Foreign Application Priority Data

Aug. 20, 1990 [JP] Japan .................. 2-219658

[51] Int. Cl.$^5$ .................. G01N 27/409; G01N 27/41; F02M 25/07
[52] U.S. Cl. .................. 204/424; 123/704; 204/425; 204/426; 204/427
[58] Field of Search .............. 204/424, 425, 426, 427, 204/428, 429, 153.18; 123/704

[56] References Cited

U.S. PATENT DOCUMENTS

| | | | |
|---|---|---|---|
| 4,272,329 | 6/1981 | Hetrick et al. | 204/153.18 |
| 4,772,376 | 9/1988 | Yukawa et al. | 204/410 |
| 4,823,760 | 4/1989 | Nishida | 123/571 |
| 4,938,861 | 7/1990 | Kurosawa et al. | 204/425 |
| 4,990,235 | 2/1991 | Chujo | 204/424 |

FOREIGN PATENT DOCUMENTS

| | | |
|---|---|---|
| 60-138263 | 7/1985 | Japan . |
| 61-247839 | 11/1986 | Japan . |
| 62-3094 | 8/1987 | Japan . |
| 2223856 | 9/1990 | Japan . |

OTHER PUBLICATIONS

SAE 880133, Closed Loop Control Of The EGR Rate Using The Oxygen Sensor, Mar. 1988.

Primary Examiner—John Niebling
Assistant Examiner—William T. Leader
Attorney, Agent, or Firm—Cushman, Darby & Cushman

[57] ABSTRACT

An oxygen concentration detecting apparatus having, a pumping cell and a sensing cell, electrodes formed on both surfaces of each of the pumping and sensing cells, a related support structure forming a closed space by being connected with the pumping and sensing cells, an opening communicating between the closed space and the surrounding environment, an electromotive force detector for detecting an electromotive force generated between the electrodes of the sensing cell, a voltage source for applying a voltage between the electrodes of the pumping cell, a current detector for detecting as a signal representing the oxygen concentration a current flowing in the pumping cell when a voltage is applied between the electrodes of the pumping cell, and a controller for controlling the voltage so that the electromotive force is constant at a specified value at which value the above-mentioned current is 70% or less of the limiting current.

6 Claims, 9 Drawing Sheets

OXYGEN CONCENTRATION DETECTING APPARATUS

This is a continuation of application Ser. No. 07/747,030, filed on Aug. 19, 1991, which was abandoned upon the filing hereof.

BACKGROUND OF THE INVENTION

This invention relates to an oxygen concentration detecting apparatus, and more particularly to an oxygen concentration using an oxygen ion conduction type solid electrolyte.

Conventionally, there has been a prior art apparatus for controlling an electromotive force, generated in a sensing cell, at a specified value, and detecting an oxygen concentration from a value of current flowing in a pumping cell. There has been another prior art apparatus for limiting the above-mentioned current value to 80% of the limiting current to ensure a longer durability of the sensor in the above-mentioned detection (SAE880133, for example).

However, when an apparatus mentioned above for detecting an oxygen concentration from a current value of 80% of the limiting current is used in an intake pipe, since the oxygen concentration of the suction pipe is higher than that of the exhaust pipe, the pumping current shifts in a large measure to a higher side of oxygen concentration by a pressure pulsation in the intake pipe. This makes it impossible to detect the oxygen concentration with high accuracy, so that emission increases and the emission cannot be limited within the regulated value.

SUMMARY OF THE INVENTION

This invention has as its object to detect the oxygen concentration in the in take pipe and prevent the emission from deteriorating.

As means for solving the above problem, this invention proposes an oxygen concentration detecting apparatus comprising:

a pumping cell and a sensing cell each comprising a solid electrolyte capable of conducting oxygen ions;

electrodes formed on both surfaces of each of the pumping and sensing cells;

a related support structure forming a closed space by being connected with the pumping and sensing cells;

an opening communicating between the closed space and the surrounding environment in such a manner that the oxygen partial pressure of the closed space has a tendency to become equal to the oxygen partial pressure in the surrounding environment;

electromotive force detecting means for detecting an electromotive force generated between the electrodes of the sensing cell;

a voltage source for applying a voltage between the electrodes of the pumping cell;

current detecting means for detecting as a signal representing the oxygen concentration a current flowing in the pumping cell when a voltage is applied between the electrodes of the pumping cell; and control means for controlling the above-mentioned voltage so that the above-mentioned electromotive force becomes constant at a specified value at which value the above-mentioned current is 70% or less of the limiting current.

By the above means, the electromotive force produced between the electrodes of the sensing cell is detected, and the voltage applied to the pumping cell is controlled so that the electromotive force becomes constant. At this time, the pumping current flowing in the pumping cell is detected as a signal representing the oxygen concentration. The pumping current is limited to 70% or less of the limiting current, and a shift of the pumping current is limited to a low value.

By this invention, a shift amount of the shift of the pumping current is limited to 1% or less by limiting the pumping current to 70% or less of the limiting current, and therefore, it is possible to detect the oxygen concentration with high accuracy from a pumping current value, restrain the emission from deteriorating and thereby limit the quantity of emission within a regulated value.

BRIEF DESCRIPTION OF THE DRAWINGS

The above and other objects and advantages of the present invention will become apparent by reference to the following description and accompanying drawings wherein.

DESCRIPTION OF THE PREFERRED EMBODIMENTS

Embodiments of this invention will be described with reference to the accompanying drawings.

Figure 1:
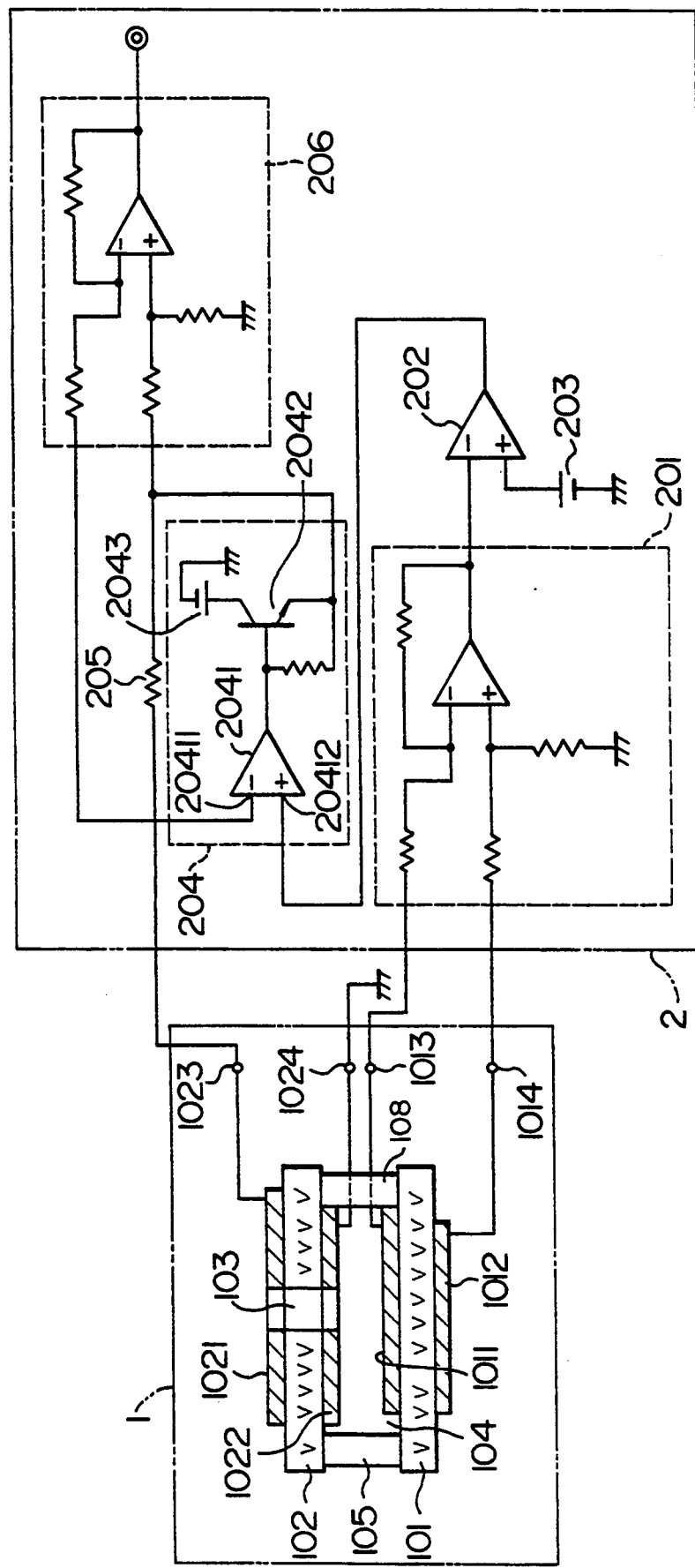
FIG. 1 is a construction diagram showing the overall construction of an embodiment of this invention.

FIG. 1 is a construction diagram showing the overall construction of a first embodiment of this invention.

Reference numeral 1 indicates a sensor for detecting the oxygen concentration and 2 indicates a detection circuit for detecting signals from the sensor 1. A sensing cell 101 and a pumping cell 102 both comprise an oxygen ion conduction type solid electrolyte such as zirconia or the like in a plate form. Those cells are covered on their top and bottom sides with porous thin-film precious metal electrodes 1011, 1012, 1021, and 1022

(platinum, for example). Terminals 1013, 1014, 1023, and 1024 are connected to the electrodes 1011, 1012, 1021, and 1022. The sensing cell 101 and the pumping cell 102 are placed facing each other with interposition of spacers 105 and 108, thus forming a closed space 104 (hereafter referred to as the chamber).

In the pumping cell 102, there is provided an opening 103 for introducing air into the chamber 104.

The construction of the sensor 1 will be described later in detail.

Reference numerals 201, 206 indicate differential amplifiers, 202 a voltage comparator, 203 a reference voltage source, 204 an applied voltage control circuit, and 205 a current detecting resistance. The applied voltage control circuit 204 comprises a voltage comparator 2041, an NPN transistor 2042, and a power source 2043. The output of the voltage comparator 2041 is connected to the base of the transistor 2042, and the power source 2043 to the collector of the transistor 2042.

Figure 2:
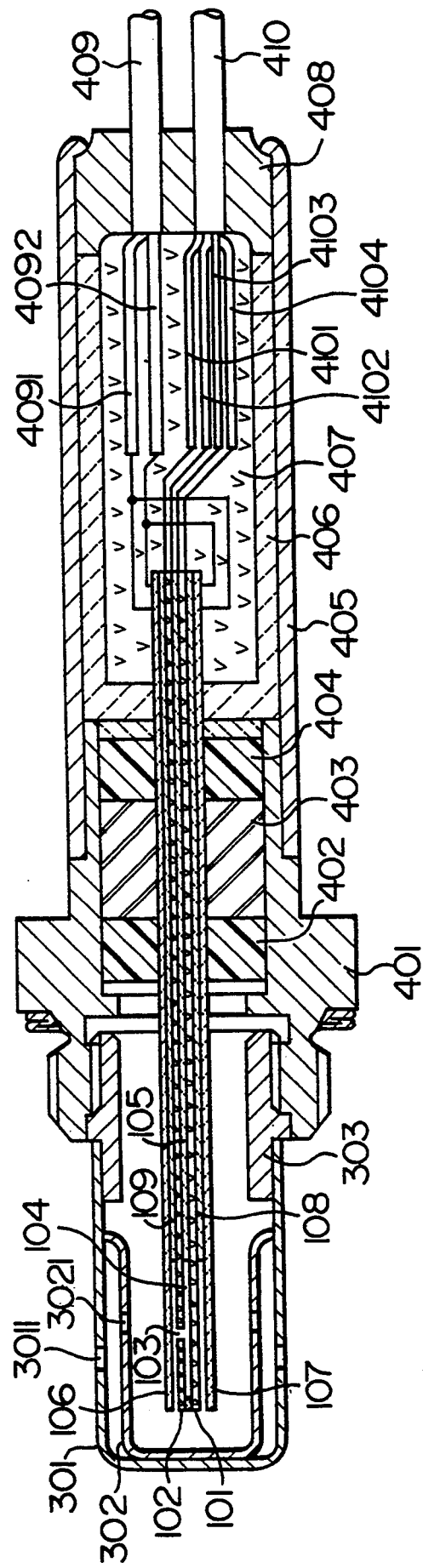
FIG. 2 is a sectional view of an 02 sensor.

FIG. 2 is a sectional view of the $O_2$ sensor including the sensor 1.

The $O_2$ sensor comprises an outer cover 301, an inner cover 302, a cover holder 303, a housing 401, inorganic adhesives 402, 404, glass 403, a conductor housing 405, a connector holder 406, a connector 407, a connector end 408, a heater terminal 409, an electrode terminal 410, a sensing cell 101, a pumping cell 102, an opening 103, a chamber 104, spacers 105, 108, and 109 and heaters 106 and 107. Gas introducing ports 3011 and 3021 are provided in specified numbers and at equal intervals at the outer peripheries of the outer cover 301 and the inner cover 302. The gas introducing ports 3021 are provided at positions closer to the housing 401 than the gas introducing ports 3011. The heater terminal comprises a heater high voltage conductor 4091 and an earthing conductor 4092. Those conductors are connected to both ends of heating wires (not shown) printed on the heaters 106 and 107 made of an electrical insulating material. The electrode terminal 410 comprises a pumping cell high voltage conductor 4101, a pumping cell earthing conductor 4102, a sensing cell earthing conductor 4103, and a sensing cell high voltage conductor 4104. Those conductors are connected to the terminals 1023, 1024, 1013 and 1014 shown in FIG. 1.

The sensing cell 101 and the pumping cell 102 are placed against the heaters 106 and 107 with interposition of the spacers 108 and 109. The heaters 106 and 107 are used to heat the sensing cell 101 and the pumping cell to a high temperature of at least 600° C. or higher to reduce their impedances.

Power is supplied to the heaters 106 and 107 to heat the sensing cell 101 and the pumping cell 102, and a voltage is applied between terminals 1023 and 1024 to conduct a current in the pumping cell 102. Then, at the electrode 1022, an electrochemical reaction occurs as follows:

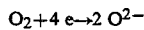

$$O_2 + 4e \rightarrow 2 O^{2-}$$

By this reaction, oxygen is injected into the pumping cell 102.

On the other hand, at the electrode 1021, oxygen is discharged by the following reaction:

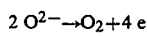

$$2 O^{2-} \rightarrow O_2 + 4e$$

This is known as the oxygen pumping action.

The current required for the oxygen pumping action is called the pumping current.

By the above-mentioned oxygen pumping action, the oxygen concentration is made lower in the chamber 104 than outside the chamber 104.

At this time, the since oxygen concentration differs between the two end faces of the sensing cell 101, concentration cell action causes an electro-motive force to be generated between the terminals 1013 and 1014 of the sensing cell 101.

Figure 3:
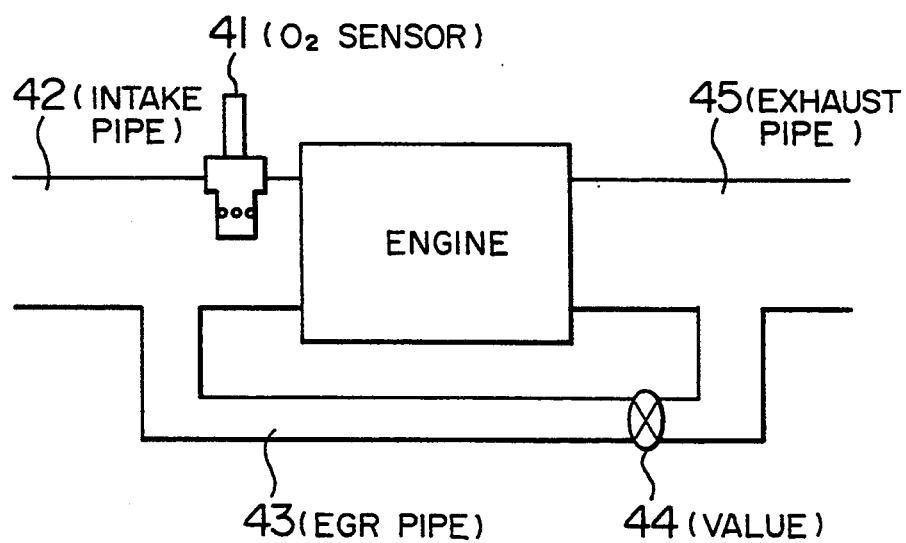
FIG. 3 is a schematic construction diagram showing the 02 sensor which has been mounted.

FIG. 3 shows the mounted condition of the $O_2$ sensor in an exhaust gas recirculation unit (EGR unit) according to this embodiment. An $O_2$ sensor 41 is mounted on the down stream side (between the outlet of the EGR pipe 43 and the engine) of the intake pipe 42. The EGR unit detects an EGR rate from the $O_2$ density detected by the $O_2$ sensor 41. The EGR pipe 43 communicates between the exhaust pipe 45 and the intake pipe 42. The exhaust gas is recirculated through the EGR pipe 43 to the intake pipe 42.

A valve 44 to adjust the recirculated quantity of the exhaust gas is installed in the EGR pipe 43.

Figure 4:
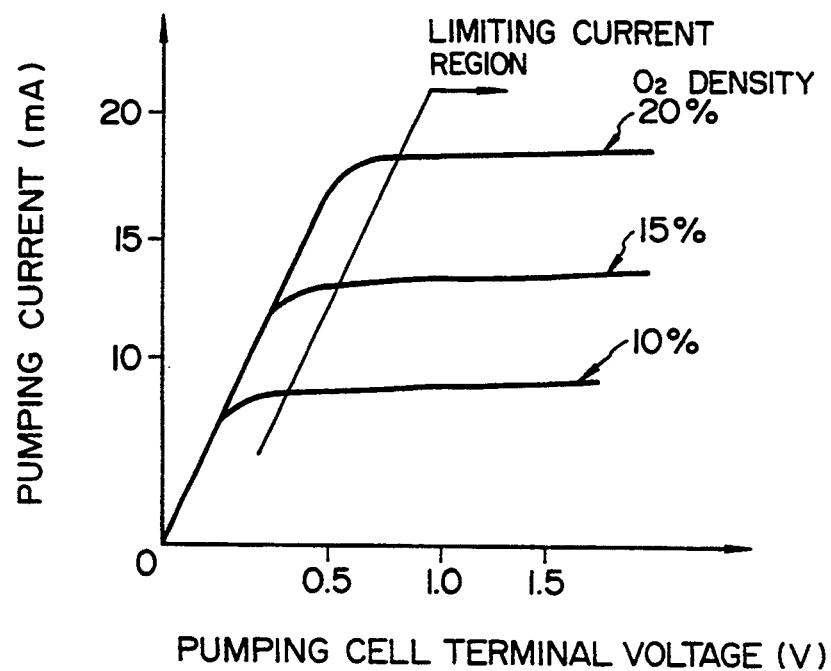
FIG. 4 is a characteristic diagram showing the relation between the pumping current and the pumping cell terminal voltage.

FIG. 4 shows the relation between a voltage applied across the terminals 1023 and 1024 of the pumping cell 102 and the pumping current.

As is clear from FIG. 4, in the limiting current region where the pumping current is saturated, pumping current values are substantially constant when they reach their limiting current values even though the pumping cell terminal voltage is controlled roughly. For this reason, $O_2$ concentration can be measured from limiting current values.

Therefore, it has been a general practice to measure $O_2$ concentration from a limiting current value of 80% of the limiting current value to obtain a longer durability of the sensor.

Figure 5:
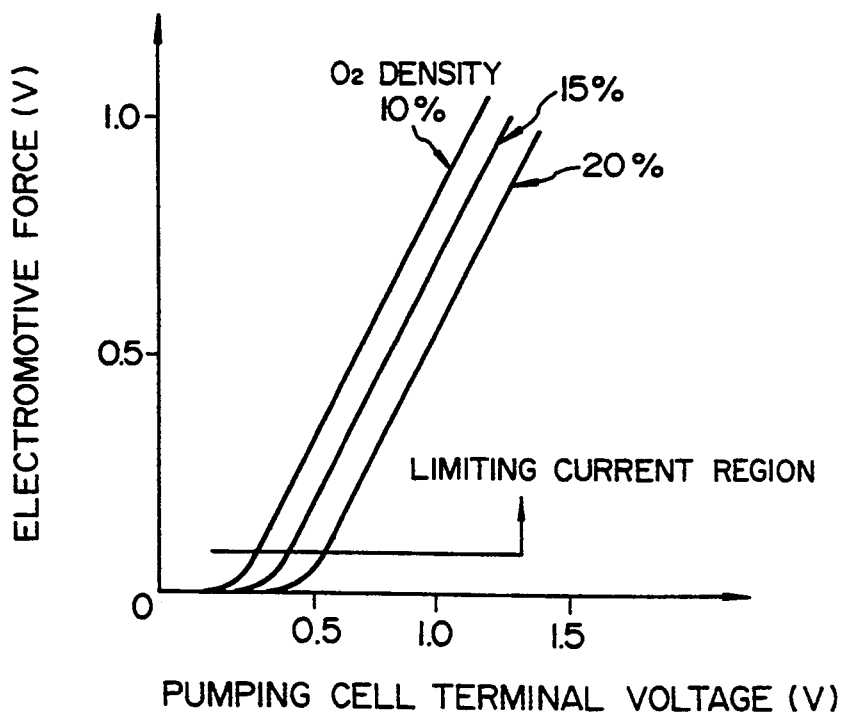
FIG. 5 is a characteristic diagram showing the relation between the electromotive force and the pumping cell terminal voltage.
Figure 6:
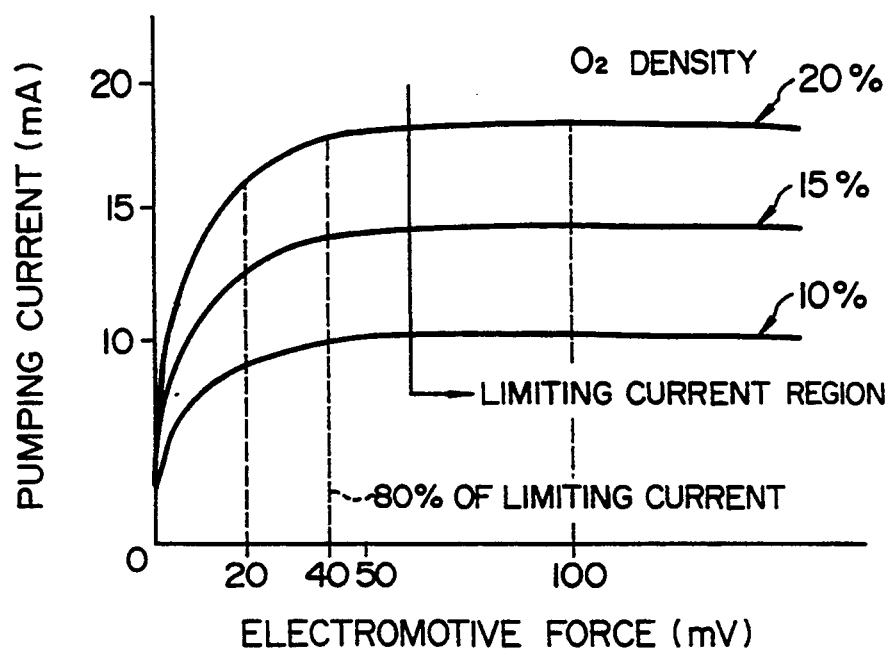
FIG. 6 is a characteristic diagram showing the relation between the pumping current and the electromotive force.

Furthermore, as shown in FIG. 5, in a region around the limiting current, the electromotive force increases sharply with respect to the voltage applied between the terminals of the pumping cell 102. Therefore, $O_2$ concentration has heretofore been measured from the pumping current under the condition that the electromotive force is kept at a fixed value of 40 mV at which the pumping current is 80% of the limiting current as shown in FIG. 6.

However, if a current which is 80% of the limiting current is conducted in the pumping cell, the oxygen concentration becomes extremely low in the chamber 14. If an $O_2$ sensor is installed in the intake pipe, when the pressure in the intake pipe rises promptly, a gas with a high oxygen concentration flows into the chamber 104, thus increasing the pumping current. Conversely, when the pressure in the intake pipe drops promptly, a gas with an extremely low oxygen concentration flows out of the chamber 104, but the decrease in the pumping current is very small. In the intake pipe, such pressure changes repeat periodically. Hence, the pumping current shifts to a larger value than a value corresponding to the actual oxygen concentration. This makes it impossible to measure $O_2$ concentration with high accuracy.

Figure 7:
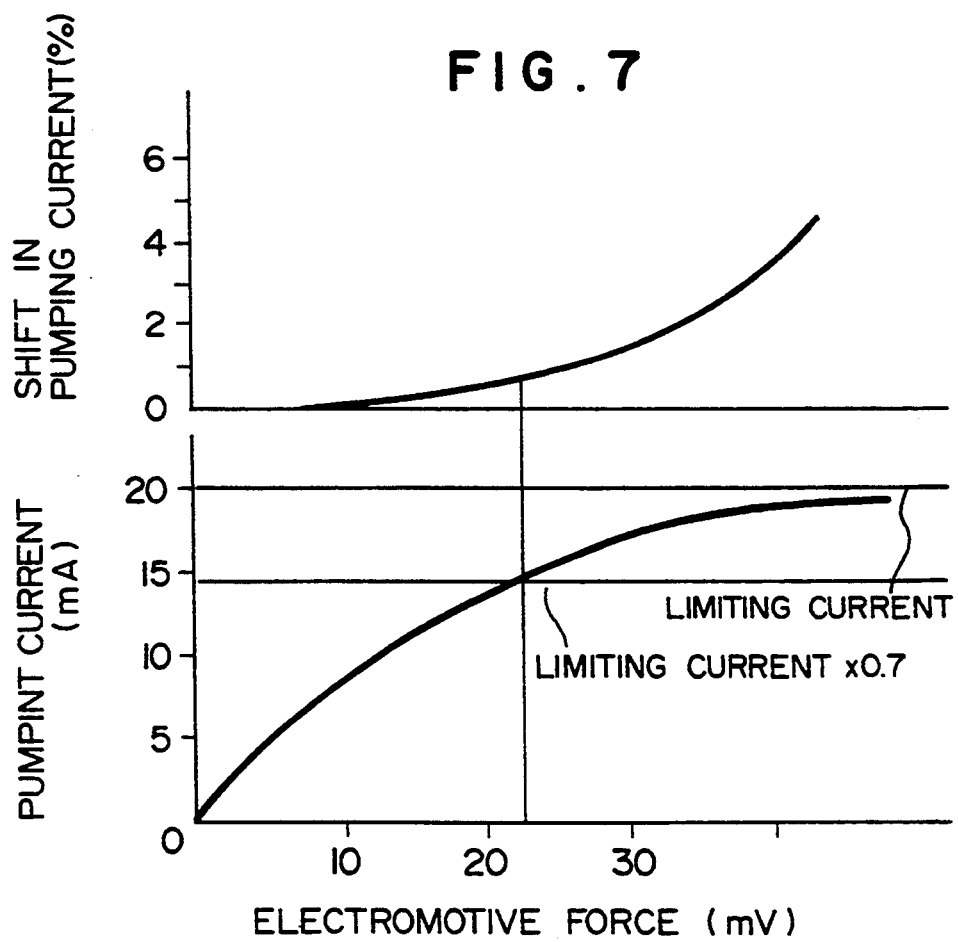
FIG. 7 is a characteristic diagram showing the relation between shifts in the pumping current and the electromotive force.

FIG. 7 shows the relation between shifts in the pumping current and the electromotive force.

The shift of the pumping current is small in the low electromotive force region, but becomes large as the pumping current approaches the limiting current. The shift can be limited to 1% or less when the pumping current is 70% or less of the limiting current.

Figure 8:
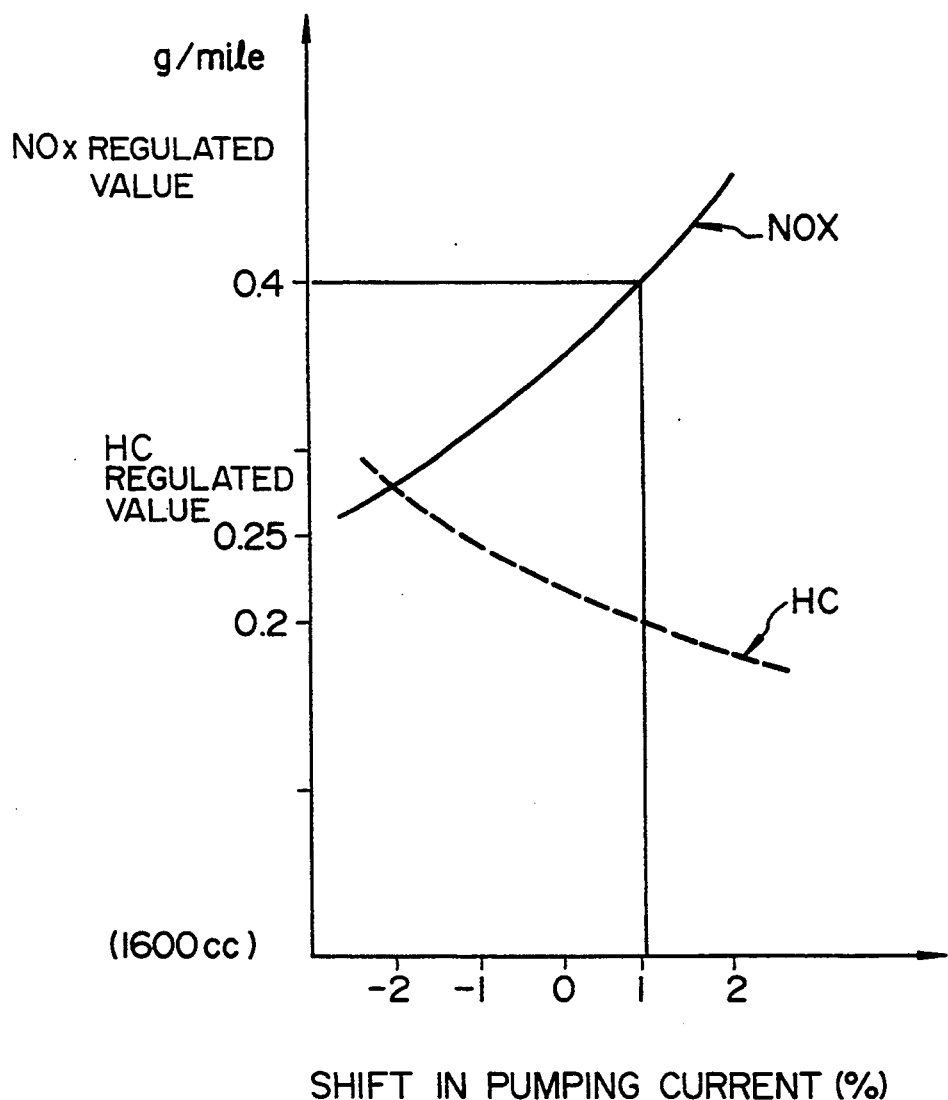
FIG. 8 is a characteristic diagram showing the relation between shifts in the pumping current and emission.

FIG. 8 shows the relation between shifts in the pumping current and emission (HC and NOx). This is the case of a 1600 cc engine. The regulated values of NOx and HC are 0.4 g/mile and 0.25 g/mile. If the regulated value of NOx were 0.7 g/mile, even when the shift is about 2%, the discharged quantity would be within the regulated value. However, when the regulation is severe and the regulated value of NOx is 0.4 g/mile, unless the shift of the pumping current is limited to 1% or less, the discharge quantity of NOx exceeds the regulated value. Therefore, it is understood that it is necessary to limit the shift of the pumping current to 1% or less.

For the reason mentioned above, according to this invention, $O_2$ concentration is measured in the region of 50% to 70% of the limiting current by limiting the electromotive force instead of using the limiting current region or 80% or the limiting current as in the prior art. In the region of less than 50% of the limiting current, a shift amount of the pumping current is small, but since a current representing $O_2$ density is small, an error is large. Accordingly, in this embodiment, the pumping current is set so as to be about 70% of the limiting current by controlling the electromotive force at 20 mV.

The operation of this invention will be described with reference to FIG. 1.

The differential amplifier 201 outputs a signal proportional to a potential difference between the terminals 1013 and 1014 of the sensing cell 101.

The output of the voltage comparator 202 falls when the output of the differential amplifier 201 rises relative to the voltage of the reference voltage source 203, and rises when the output of the differential amplifier 201 falls relative to the voltage of the reference voltage source 203.

The terminals 20411 and 20412 of the voltage comparator 204 of the applied voltage control circuit 204 are at the same voltage. However, when the electromotive force of the above-mentioned sensing cell 101 is higher than 20 mV, a signal input into the terminal 20412 becomes small and the input into the base of the transistor 2042 becomes small, so that the voltage applied to the pumping cell 102 falls. As a result, the electromotive force in the pumping cell 102 falls and is held constant at 20 mV.

Conversely, when the electromotive force of the sensing cell 101 is lower than 20 mV, a signal input into the terminal 20412 becomes large, and the input into the base of the transistor 2042 becomes large, so that the voltage applied to the pumping cell 102 rises. Consequently, the electromotive force in the pumping cell 102 rises, and is held constant at 20 mV.

The pumping current at a constant electro-motive force flows to the current detecting resistance 205, and the differential amplifier 206 outputs a signal proportional to a potential difference across the current detecting resistance 205. From this signal, $O_2$ concentration is measured. Incidentally, the voltage of the reference voltage source 203 is set at a value (0.2 V), which is obtained by multiplying an electromotive force (20 mV, in this embodiment) when the pumping current is 70% or less of the limiting current by an amplification factor (10, for example) of the differential amplifier 201. Therefore, the electromotive force in the pumping cell 102 is becomes constant at 20 mV, so that the pumping current does not exceed 70 of the limiting current. This makes it possible to limit a shift in the pumping current to less than 1%.

Figure 9:
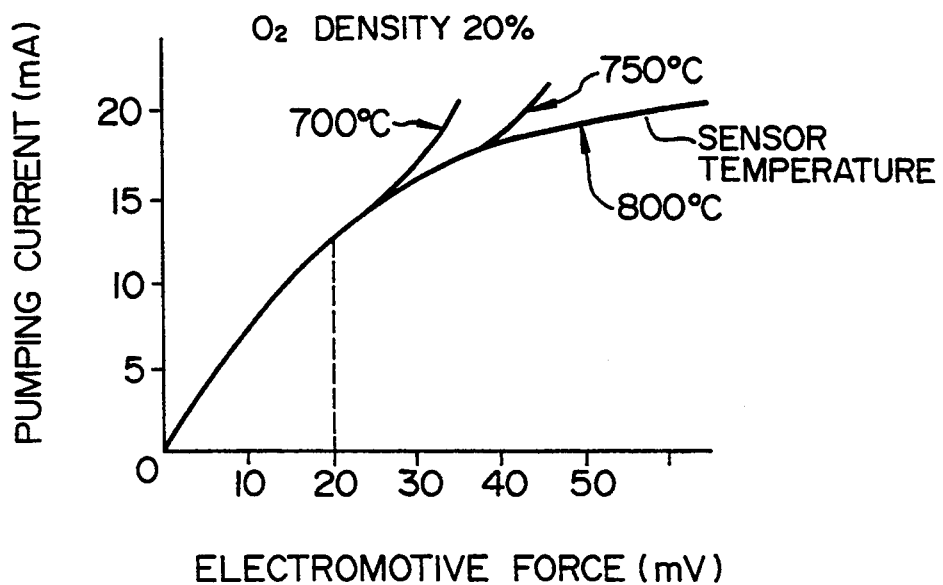
FIG. 9 is a characteristic diagram showing the relation between the pumping current and the electromotive force at different temperatures.

FIG. 9 shows the relation between the pumping current and the electromotive force at different sensor temperatures. As indicated in FIG. 9, as the sensor temperature becomes low, the electromotive force does not rise sufficiently, and in the limiting current region at an electromotive force of 50 mV or higher, a large error occurs, so that $O_2$ concentration cannot be detected from a pumping current value. However, at an electromotive force of around 20 mV, an error is small even when the sensor temperature is low, and therefore, $O_2$ concentration can be detected from a pumping current value. Accordingly, if the electromotive force is controlled a constant value of around 20 mV, $O_2$ concentration can be detected even when the sensor temperature is low.

Figure 10:
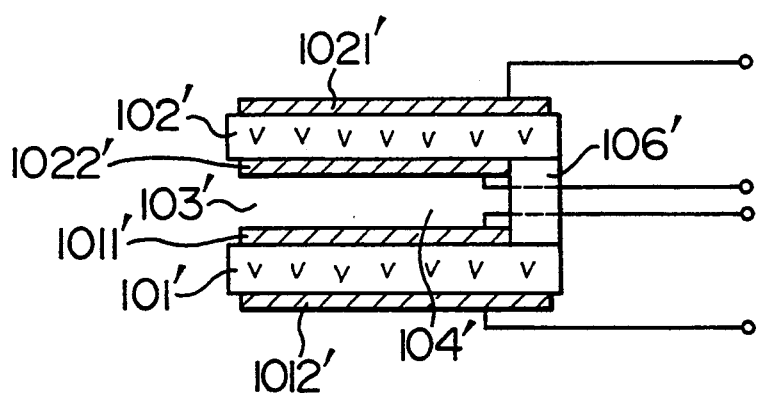
FIG. 10 is a sectional view showing a cross section of the essential part of a sensor having a pumping cell and a sensing cell with a slit between those cells.

Instead of the sensor 1 shown in FIG. 1, a sensor may be used which is of a construction as depicted in FIG. 10. A sensing cell 101' and a pumping cell 102' have electrodes 1011', 1012' and 1021', 1022' formed respectively on their surfaces. The sensing cell 101' and the pumping cell 102' are placed facing each other with a gap of several tens to several hundreds of microns provided between them, thus forming a closed space 104' (chamber). An opening 103' for introducing air into the closed space 104' is formed at the extreme ends of the pumping cell 102 and the sensing cell 101. In the above description of the embodiment, a case was shown in which a pumping cell and a sensing cell are used. A solid electrolyte may be used which serve both as the pumping cell and the sensing cell.

Figure 11:
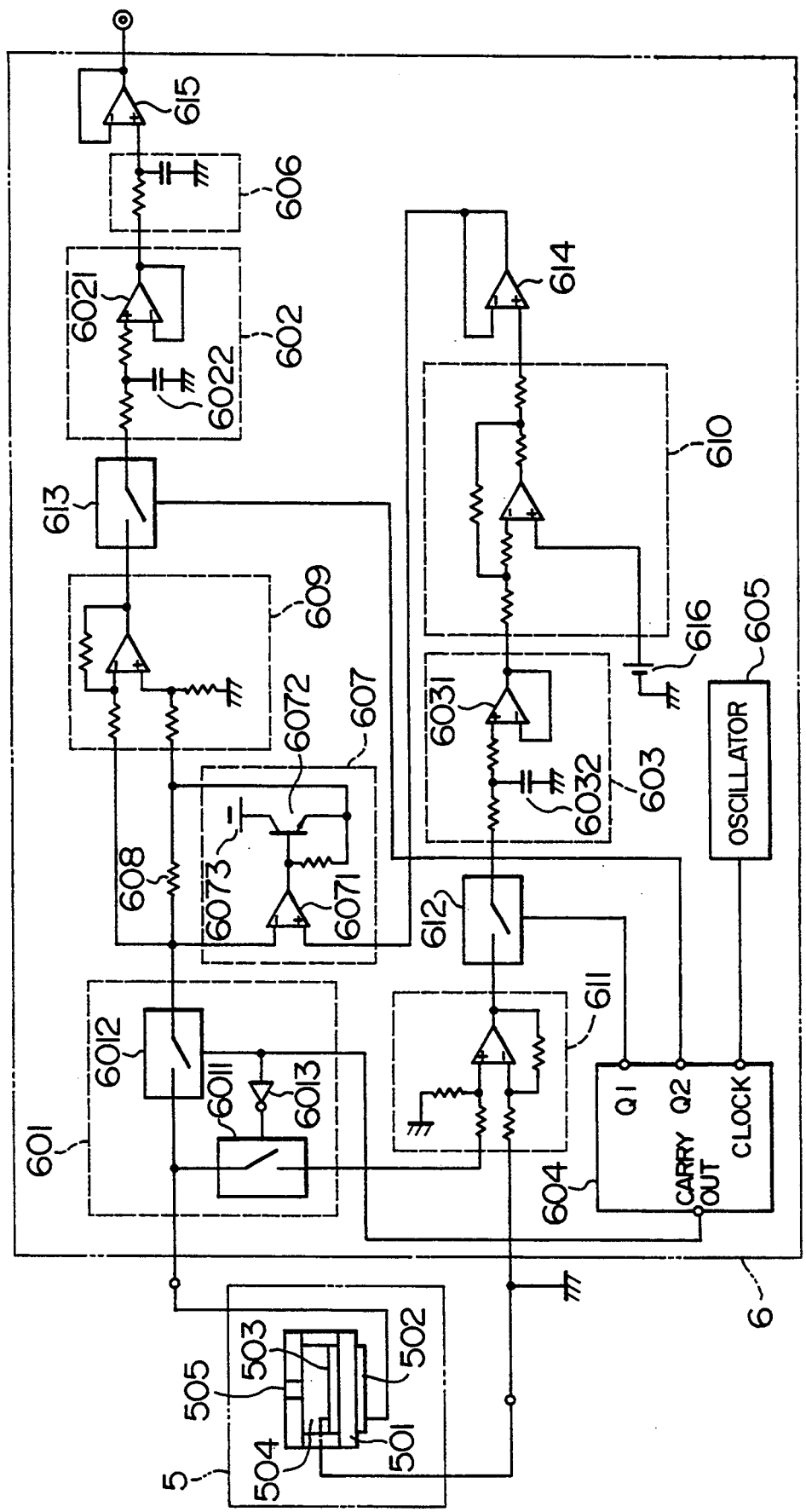
FIG. 11 is a construction diagram showing an overall construction of another embodiment using a solid electrolyte which serves as both a sensing cell and a pumping cell.

Referring to FIG. 11, description will be made of an embodiment in which a solid electrolyte is used both as the pumping cell and the sensing cell.

A sensor 5 comprises a solid electrolyte 501 used both as the pumping cell and the sensing cell, electrodes 502, 503 formed on the surfaces of the solid electrolyte 501, a closed space (chamber) 504, and an opening 505 for introducing air into the chamber 504.

Reference numeral 6 indicates a detection circuit for detecting a signal from the sensor 5.

A switching circuit 601 comprises bi-directional switches 6011, 6012, and an inverter 6013. Sample and hold circuits 602, 603, comprising operational amplifiers 6021, 6031 and capacitors 6022, 6032, respectively, hold input signals.

Reference numeral 605 indicates an oscillator and 604 indicates a counter, the operation of which counter will be described later, and 606 indicates a low-pass filter for removing high-frequency noise. An applied voltage control circuit 607 comprises an operational amplifier 6071, a transistor 6072, and a power source 6073. The transistor 6072 outputs a current corresponding to output of the operational amplifier. Reference numeral 608 indicates a current detecting resistance, 609, 611 differential amplifiers, 610 a voltage comparator, 612, 613 bi-directional switches, and 614, 615 buffers. Reference numeral 616 indicates a reference voltage source, and its output voltage is set to be smaller than a value obtained by amplifying the electromotive force generated owing to the concentration cell action between the electrodes 502 and 503 by an amplification factor of the differential amplifier 411. In this embodiment, since the electromotive force is controlled at a constant level of 20 mV, when the amplification factor is 10, the reference voltage is 0.2 V.

The operation of the counter will be described in the following.

Figure 12:
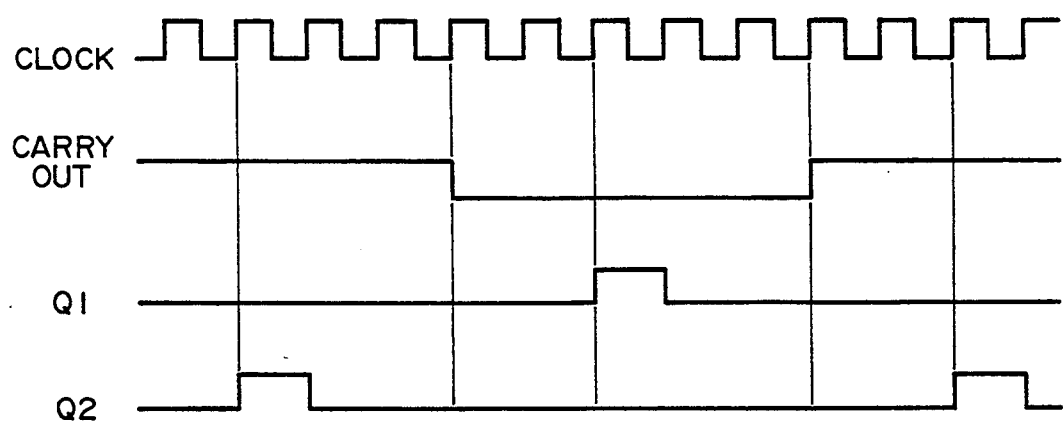
FIG. 12 is a time chart showing outputs of the counter 604 shown in FIG. 10.

When a signal is applied to the CLOCK terminal of the counter 604, signals shown in FIG. 12 are outputted from the CARRY OUT, Q2, and Q1 terminals of the counter 604.

When the output of the CARRY OUT terminal is HIGH, the bi-directional switch 6011 is open and the bi-directional switch 6012 is closed. At this time, a current flows to the solid electrolyte 501 through the transistor 6072, the current detecting resistance 608, and bi-directional switch 6012, the oxygen pumping action takes place, with the result that an electromotive force is generated between the electrodes 502 and 503. On the other hand, when the output of the CARRY OUT terminal is LOW and the output of the terminal Q1 is HIGH, the bi-directional switches 6011 and 612 are closed and the bi-directional switch 6012 is open. At this time, a voltage is not applied to the solid electrolyte 501 from outside, the electromotive force is a potential difference between the electrodes 502 and 503, and is detected by the differential amplifier 611. The amplified electromotive force signal passes through the bi-directional switch 612, is held by the sample and hold circuit 603, and is compared with the voltage of the reference voltage source 616 by the voltage comparator 610.

The output of the voltage comparator 610 becomes low when the electromotive force signal is higher than the reference voltage, and becomes high when the electromotive force signal is lower than the reference voltage. When the output of the CARRY OUT terminal goes HIGH again, the bi-directional switch 6012 is closed, and the oxygen pumping action of the solid electrolyte 501 is resumed.

At this time, when the above-mentioned electromotive force signal is high, the output of the voltage comparator 610 becomes low, and therefore, the voltage applied to the solid electrolyte 501 becomes low. On the other hand, when the electromotive force signal is low, the voltage applied to the solid electrolyte 501 becomes high. By repetition of the above operations, the electromotive force of the solid electrolyte 501 is held constant at 20 mV.

When the outputs of the CARRY OUT terminal and the Q2 terminal are HIGH, the bi-directional switches 6012 and 613 are closed, and the pumping current is detected by the differential amplifier 609 as a potential difference across the current detecting resistance 608, is held by the sample and hold circuit 602, and is outputted through the low pass filter 606 and the buffer 615.

While particular embodiments of the present invention have been shown and described, it will be obvious to those skilled in the art that various changes and modifications may be made without departing from the present invention in its broader aspects.

What is claimed is:

1. An oxygen concentration detecting apparatus for an internal combustion engine, comprising:
   an intake pipe, an exhaust pipe, and an exhaust gas recirculation pipe, connecting between said exhaust pipe and a first area of said intake pipe;
   a sensor comprising a pumping cell and a sensing cell each comprising a solid electrolyte capable of conducting oxygen ions including electrodes formed on surfaces of each of said pumping and sensing cells, said sensor located in the intake pipe downstream of and near said first area to detect an oxygen concentration in an intake air/exhaust air mixture therein;
   a support structure, connected with said pumping and sensing cells to form a closed chamber therein;
   an opening portion for communicating between said closed chamber and its surrounding environment in such a manner that the oxygen partial pressure of said closed space has a tendency to become equal to the oxygen partial pressure in the surrounding environment;
   electromotive force detecting means for differentially detecting and amplifying an electromotive force generated between the electrodes of said sensing cell to produce an amplified electromotive force signal;
   a voltage source for applying a voltage between the electrodes of said pumping cell;
   a current detecting means for detecting a current flowing in said pumping cell as a signal representing the oxygen concentration when a voltage is applied between the electrodes of said pumping cell; and
   control means, receiving the amplified electromotive force signal, for controlling said voltage source to maintain said electromotive force at a specified value at which value said current flowing in said pumping cell is 70% or less of a limiting current of said sensor, which is a value at which current flowing in said pumping cell saturates when the voltage is applied between the electrodes of said pumping cell.

2. An oxygen concentration detecting apparatus according to claim 1, wherein said control means comprises comparing means for comparing an electromotive force detected by said electromotive force detecting means with a predetermined voltage value and setting means for controlling said voltage source to set the magnitude of said voltage so that said current is a specified value within 50% to 70% of the limiting current according to a comparison result by said comparing means.

3. A detecting apparatus as in claim 1 further comprising a value, in said exhaust gas recirculation pipe, for selectively opening and closing communication between said exhaust pipe and said intake pipe through said exhaust gas recirculation pipe.

4. An oxygen concentration detecting apparatus for an internal combustion engine comprising:
   an intake pipe, an exhaust pipe, and an exhaust gas recirculation pipe, connecting between said exhaust pipe and a first area of said intake pipe;
   a plate-shaped solid electrolyte capable of conducting oxygen ions, said sensor located in the intake pipe downstream of and near said first area to detect an oxygen concentration in an intake air/exhaust air mixture therein;
   first and second electrodes formed on surfaces of said solid electrolyte;
   a support structure connected to said solid electrolyte to form a closed chamber therewithin;
   an opening portion for communicating between said closed chamber and its surrounding environment in such a manner that the oxygen partial pressure of said closed space has a tendency to become equal to the oxygen partial pressure of the surrounding environment;
   electromotive force detecting means for differentially detecting and amplifying an electromotive force generated between said first and second electrodes in a first period to produce an amplified electromotive force signal;

a power source for applying a voltage between said first and second electrodes in a second period;

current detecting means for detecting a current flowing in said solid electrolyte in the second period as a signal representing the oxygen concentration; and control means for controlling said power source to maintain said electromotive force constant at a specified value, at which value said current is 70% or less of a limiting current of said electrolyte, wherein said limiting current is a value at which current flowing in said pumping cell saturates when the voltage is applied between the first and second electrodes;

wherein said first and second periods alternate.

5. An oxygen concentration detecting apparatus according to claim 4, wherein said control means comprises comparing means for comparing an electromotive force detected by said electromotive force detecting means with a predetermined voltage vale and setting means for controlling said power source to set the magnitude of said voltage so that said current is a specified value within 50% to 70% of the limiting current according to a comparison result by said comparing means.

6. A detecting apparatus as in claim 4 further comprising a valve, in said exhaust gas recirculation pipe, for selectively opening and closing communication between said exhaust pipe and said intake pipe through said exhaust gas recirculation pipe.

* * * * *